United States Patent [19]
McNally

[11] Patent Number: 5,210,814
[45] Date of Patent: May 11, 1993

[54] HIGH RESOLUTION OPTICAL DEVICE WITH RIGID FIBER OPTIC BUNDLE

[75] Inventor: A. David McNally, Holden, Mass.

[73] Assignee: Precision Optics Corporation, Gardner, Mass.

[21] Appl. No.: 861,258

[22] Filed: Mar. 31, 1992

[51] Int. Cl.⁵ .............................................. G02B 6/06
[52] U.S. Cl. .................................. 385/116; 385/118; 128/6
[58] Field of Search ............... 385/116, 117, 118, 119, 385/142; 128/6, 4; 359/708

[56] References Cited

U.S. PATENT DOCUMENTS

| | | | |
|---|---|---|---|
| 4,036,218 | 7/1977 | Yamashita et al. | 128/4 |
| 4,397,524 | 8/1983 | Yoshimura et al. | 385/116 |
| 4,762,391 | 8/1988 | Margolin | 385/116 X |
| 4,776,668 | 10/1988 | Fujimoto | 385/117 |
| 4,896,941 | 1/1990 | Hayashi et al. | 385/116 |
| 4,945,894 | 8/1990 | Kawashima | 128/6 |
| 4,961,738 | 10/1990 | Mackin | 128/6 |
| 4,993,817 | 2/1991 | Hoogland | 359/708 |

*Primary Examiner*—John D. Lee
*Assistant Examiner*—Phan T. Heartney
*Attorney, Agent, or Firm*—Pearson & Pearson

[57] ABSTRACT

Improved image guides for use in endoscopes, borescopes and analogous optical viewing scopes and a method for the manufacture of such image guides. An image guide is manufactured by drawing a three-glass fiber to a minimal diameter. Plural fibers are then gathered in a bundle and heated to fuse an outer fusible cladding on adjacent fibers. The bundle then can be cut to length and the ends are polished to produce an image guide. The resulting image guide has a spatial resolution that approximates the spatial resolution from conventional optics, is rugged and simpler to manufacture than other image guides.

20 Claims, 3 Drawing Sheets

REDUCE SIZE OF OPTICAL FIBER 10.

FORM A BUNDLE 20 OF OPTICAL FIBERS 10.

FUSE THE BUNDLE 21.

CUT BUNDLE 21 TO A FINITE LENGTH AND POLISH END SURFACES 22 AND 23.

LOCATE THE BUNDLE 21 IN A SHEATH 24 TO FORM AN IMAGE GUIDE 26.

HIGH RESOLUTION OPTICAL DEVICE WITH RIGID FIBER OPTIC BUNDLE

BACKGROUND OF THE INVENTION

1. Field of the Invention

This invention generally relates to optical devices and a method for making such devices. More particularly this invention is related to devices for viewing the interior of a passageway in a selective region.

2. Description of Related Art

There are a variety of applications which require an individual to view the interior of a remote chamber. In an industrial environment, for example, it is desirable to view portions of the interior of a machine, such as a jet engine, that is otherwise inaccessible. In medical applications it is desirable to view a passageway in the body. Viewing scopes that enable one to view such remote passages are well known in the art. Such devices used for mechanical applications are generally called borescopes. For medical applications the viewing scopes take many forms and are known by different names. Generically the name "endoscope" means any slender, tubular optical instrument used as a viewing system for examining an inner part of the body. In practice such viewing scopes have a variety of names, such as endoscopes, laparoscopes and bronchoscopes. In the following discussion the phrase "viewing scope" is meant to include generically both (1) borescopes and (2) endoscopes in any form including laparoscopes, bronchoscopes, etc.

Viewing scopes generally have an eyepiece at a proximal end, an objective lens at a distal end and an image guide interposed between the eyepiece and the objective lens. The image guide uses two general forms of optics, namely: rigid optics and fiber optics. Image guides using rigid optics include relay or rod lenses to transfer an image from a distal end of the viewing scope to its proximal end. The following patents disclose examples of image guides using such rigid optics:

U.S. Pat. No. 4,036,218 (1977) Yamashita et al
U.S. Pat. No. 4,993,817 (1991) Hoogland Image guides using fiber optics generally interpose a bundle of optical fibers between the proximal and distal ends of the viewing scope. The following patents disclose image guides that incorporate such fiber optics:

U.S. Pat. No. 4,776,668 (1988) Fujimoto
U.S. Pat. No. 4,938,205 (1990) Nudelman
U.S. Pat. No. 4,945,894 (1990) Kawashima
U.S. Pat. No. 4,961,738 (1990) Mackin The Fujimoto patent discloses a viewing scope with a coherent fiber optic bundle as an image guide. Each fiber comprises a pure quartz silica strand coated with a reflective layer. This patent discloses structure eliminating differential expansion between the fiber optic bundle and other portions of the viewing scope during flexure.

The Nudelman patent discloses an endoscope that includes a fiber optic bundle between distal and proximal ends. The fiber optic bundle is flexible between the ends.

The Kawashima patent discloses an endoscope in which image guide fibers transmit an image formed at the objective to a proximal end of the endoscope.

The Mackin patent discloses an angioplasty catheter that includes a fiber optic bundle for conveying an image between the distal and proximal ends.

Conventionally fiber optic bundles used in such image guides comprise a preferred three-glass fiber or two-glass fiber. A three-glass fiber has a glass core that acts as a light transmitter, a concentric reflective layer and a fusible, acid soluble outer layer. In conventional processing, a bundle of such fibers are assembled together and heated to fuse just the outer layer. Then the ends are isolated and the entire structure is immersed in an acid bath as a leaching solution to remove portions of the fusible glass between the ends so the bundle will be flexible along its length. It is difficult to control this leaching process. If the leaching continues for too long a time, the solution acid can etch through the outer glass layer and the reflective layer thereby detracting from the image by lowering its contrast. This leaching step effectively controls the minimum diameter of the individual fibers and the number of individual fibers that can be formed into a bundle of a given size. As the diameter of the fibers becomes smaller, the effort required to control the leaching process increases because the fusible layer becomes thinner. Consequently costs increase because the manufacturing is more difficult and because production yields decrease.

Optical fibers used in two-glass fiber optic bundles have a light transmitting core and a reflective outer cladding. Multiple drawing steps can reduce the light transmitting core to under 10 microns. During each drawing step a bundle of fiber passes through a die that reduces both its core and cladding and that causes the bundles and fibers within each bundle to adhere. When such fibers are drawn below 10 microns, however, the cladding becomes very thin and transmissive. Cross talk can occur and limit the contrast resolution of the viewed image. In some situations this requires the insertion of black glass or other barriers to prevent light from one fiber from transferring to another fiber through the thin cladding.

The basic criteria for selecting rigid optics or fiber optics for an image guide include spatial resolution as a primary criteria and contrast resolution, cost and ruggedness. Rigid optics provide the best spatial and contrast resolution. However, they are fragile and have the highest manufacturing costs. An image guide must be designed separately for each combination of a viewing scope length and diameter. Fiber optics, on the other hand, provide a rugged image guide and require less design effort and have lower costs. However, image guides using fiber optic bundles have limited spatial resolution. In viewing scopes of the type contemplated by this invention, the spatial resolution is limited to 5,000 to 30,000 pixels in an image. Fiber optics also provide somewhat lower contrast resolution than rigid optics and require an inventory of one bundle for each combination of viewing scope diameter and length.

SUMMARY

It is an object of this invention to provide an image guide for a viewing scope that achieves essentially the same spatial resolution as rigid optics, but uses optical fibers.

Another object of this invention to provide an image guide or viewing scope that presents an image with essentially the same spatial resolution as an image guide using rigid optics at a cost that can be even less than the cost of image guides using fiber optics.

Still another object of this invention is to provide a viewing scope with a fiber optic image guide of a given length formed from an indefinite length of a fiber optic bundle.

Still another object of this invention is to provide a viewing scope with an image guide that is rugged and less susceptible to breakage than image guides using rigid optics, but providing a spatial resolution approaching that of image guides with rigid optics.

In accordance with one embodiment of this invention, an image guide comprises a bundle of individual optical fibers. Each fiber has an inner light transmitting core and a concentric reflective layer. A rigid encapsulating structure holds the plurality of optical fibers in an integral rigid bundle. In this form each fiber can be drawn to a much smaller diameter than is possible with conventional optical fiber construction.

In accordance with another aspect of this invention, an image guide is formed by drawing an optical glass fiber to a very small diameter. Then the individual members are formed into a bundle that is encapsulated throughout its length to provide a rigid bundle with collimation throughout the length. Polishing the ends and positioning them adjacent to optical devices completes the image guide.

In accordance with still another aspect of this invention, an optical viewing scope includes a tubular housing with an objective ends at a distal end and an optical viewing means at a proximal end. An image is transferred through from the objective lens to the optical viewing device through an image guide with a plurality of optical fibers. Each optical fiber has a central light transmitting core and an annular light reflecting layer. An encapsulating material bonds the optical fibers throughout the bundle for forming a rigid bundle.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
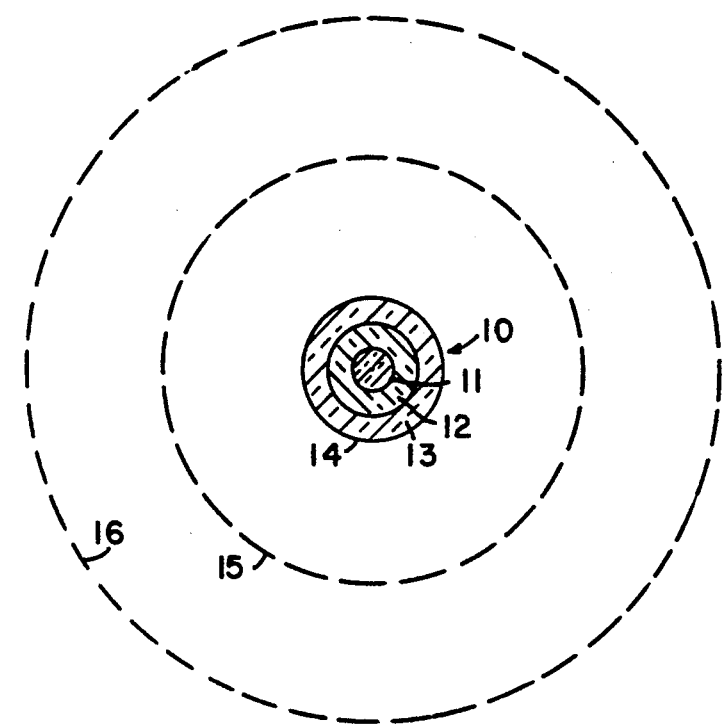
FIG. 1 depicts a cross section of an optical fiber useful in this invention and its relationship to prior art optical fibers.

FIG. 1 discloses an optical fiber 10 that is useful in accordance with this invention and is formed as a three glass fiber. The fiber 10 includes a central light transmitting core 11, a concentric reflecting layer 12 and a fusible cladding layer 13. The fusible cladding 13 provides rigidity to a single fiber and to any bundle and has a lower melting temperature than the melting temperatures for the materials in the core 11 or the reflective layer 12.

The optical fiber 10 has an outer surface 14 of a diameter that is useful in accordance with this invention. The dashed circle 15 represents the surface of larger diameter three-glass optical fibers that can be used in accordance with this invention. Three-glass fibers used in the prior art have an effective outer diameter corresponding to the surface line 16.

As previously indicated, a number of such optical fibers in the prior art are gathered in a bundle. The bundle is heated to fuse the outer cladding 13 of adjacent optical fibers together. Then the ends of the fused bundle are treated with a wax or like material in preparation for immersion in a leaching solution that chemically etches portions of the fused glass. When this process is complete, the ends of the optical bundle are rigid, but the fibers intermediate are flexible. If the etching step is not carefully controlled, the etching step can destroy the reflective layer. This can introduce cross talk between adjacent fibers and, in more extreme cases, destroy the light transmission characteristics of the fiber. Cross talk will initially tend to degrade contrast resolution and then spatial resolution.

FIGS. 2A through 2E disclose the process for forming a rigid bundle in accordance with this invention that provides greatly improved spatial resolution characteristics over conventional fiber optic bundles.

Figure 2A:
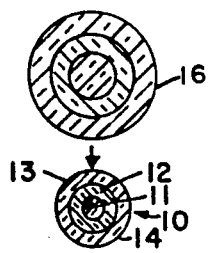
FIGS. 2A through 2E depict a sequence for converting an optical fiber into an image guide in accordance with this invention.

As disclosed in FIG. 2A the first step in accordance with the process is to reduce the size of the optical fiber 10. For example, it is possible to use conventional drawing techniques to reduce a three-glass optical fiber of the prior art having an outer diameter corresponding to the surface line 16 to a diameter that is somewhere between the surface line 14 and a surface line 15 of FIG. 1. In one specific embodiment the line 16 represents a 10-micron three-glass optical fiber. The drawing process reduces the size of that fiber to between 2 microns, corresponding to the surface 14, and 6 microns corresponding to the surface 15.

Figure 2B:
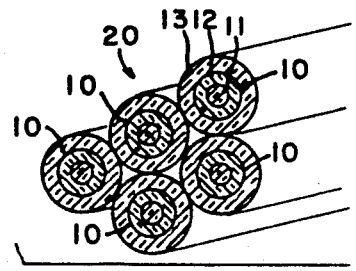

As shown in FIG. 2B the next step is to gather a plurality of these individual optical fibers 10 into a bundle with parallel optical fiber axes. In this form each fiber still retains its construction with its discrete core 11, reflective layer 12 and fusible cladding 13.

Figure 2C:
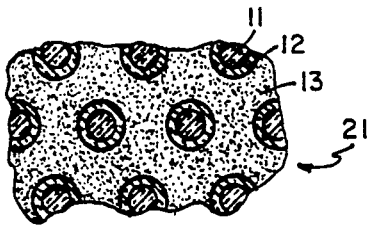
Figure 2D:
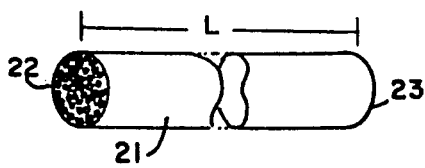

Next the material is heated to fuse the fusible cladding 13 of adjacent optical fibers. As shown in FIG. 2C, this produces a rigid bundle 21 in which the fibers retain the distinct forms of the light transmitting core 11 and the reflective core 12 in a closely packed relationship and remain collimated in the bundle 21. The distinctiveness of the discrete fusible cladding layer 13 associated with each fiber is lost, and the material encapuslates the individual fibers. This process has produced 1.1 to 1.5 mm diameter bundles 21 with up to 50,000 optical fibers. At magnifications of up to ten times, that are common in many viewing scopes, the eye does not distinguish the spatial resolution of an image of 45,000 pixels or more and an image from an rigid optic image guide.

After the rigid bundle is formed as shown in FIGS. 2A through 2C, the bundle 21 is cut, by conventional means to a finite length for a particular application. Polishing the end surfaces 22 and 23 provides a good image interface. This step, depicted in FIG. 2D, allows an optical device manufacturer to inventory bundles 21 of an indefinite length without any additional structure. The bundles may be stored with an indefinite length because the resulting bundle 21 can be cut to length L for a particular application. Thus, it is only necessary to inventory bundles of different diameters.

Figure 2E:
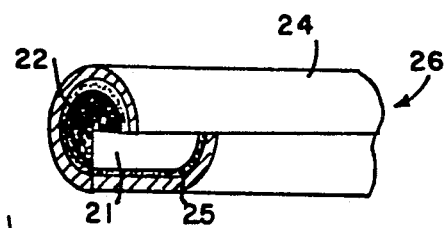

As shown in FIG. 2E the bundle 21 can be located in the sheath 24 by an epoxy or similar adhesive or bonding material 25 that is compatible with a particular application.

The resulting image guide 26 of FIG. 2E transfers an image from a distal end to a proximal end with a spatial resolution that is essentially indistinguishable from the spatial resolution of rigid optic image guides over a range of practical magnifications. The rigid bundle 21 is rugged, particularly when located within a sheath 24 as shown in FIG. 2E. The process that forms the rigid bundle 21 does not require leaching or etching steps, so the manufacturing process for rigid bundles 21 is simpler than prior art processes. As previously indicated, it is only necessary to inventory indefinite lengths of rigid bundles 21 of different diameters.

Figure 3:
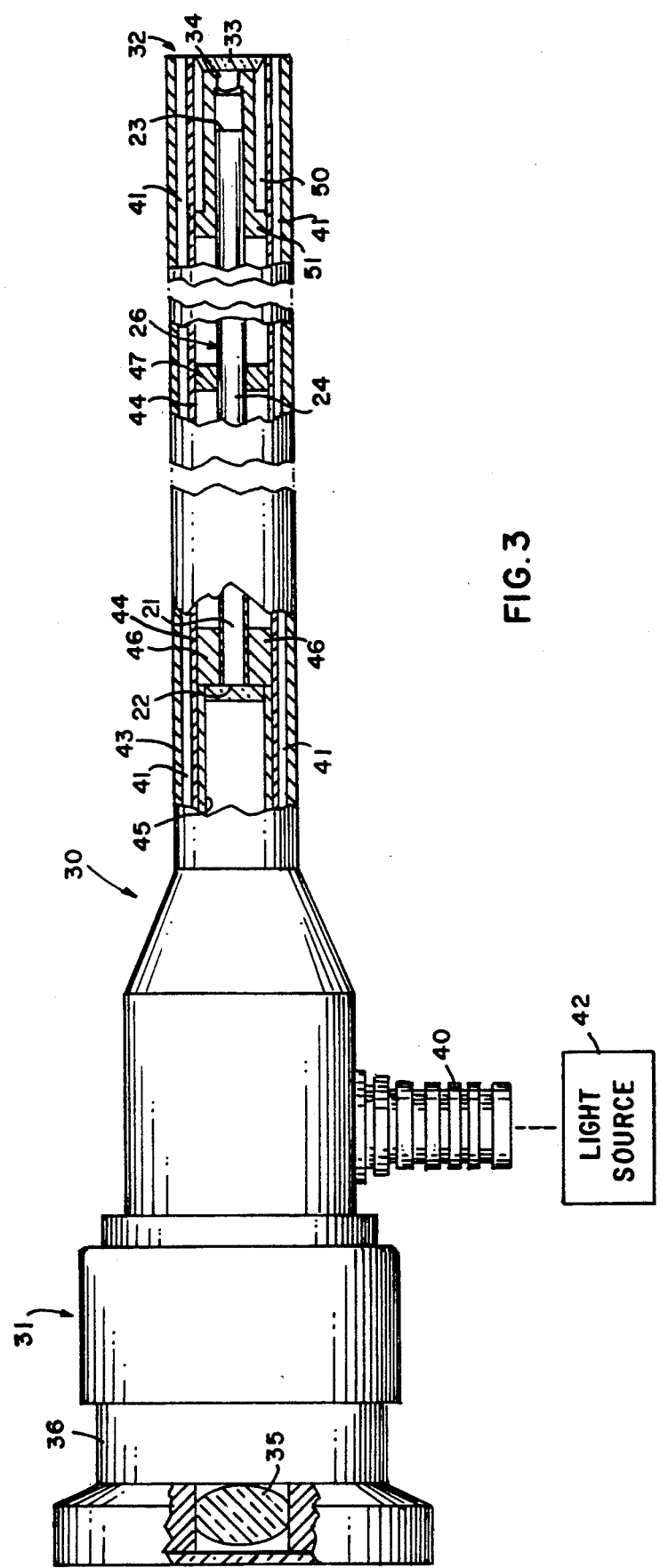
FIG. 3 is a view, partially in section, of an endoscope that utilizes this invention.

FIG. 3 discloses a viewing scope in the form of an endoscope 30 that uses the image guide 26 constructed in accordance with this invention. As shown in FIG. 3, the endoscope 30 extends between a proximal end 31 and a distal end 32. A window 33 and objective lens 34 at the distal end 32 produce an image from the field of view of the endoscope. The image guide 26 transfers this image to the proximal end, particularly to eyepiece optics such as a lens 35 at a eyepiece cup 36.

A stub fitting 40 provides a means for coupling light to transmitting optical fibers 41 from a light source 42. In this embodiment, the light fibers 41 are located in a subassembly between an outer sheath 43 and an inner sheath 44. The fibers 41 produce an annular light source at the window 33 at the distal end 32 for illuminating the object being viewed.

A lens spacer 45, that may include a relay lens or other optical element, acts as a terminus for the image guide 26. The distal end of the lens spacer 45 abuts a collar-like insert 46 at the proximal end of the image guide 26. This collar 46 supports the image guide 26 centrally of the sheath 24.

As also shown in FIG. 3, washers 47 may be positioned at intermediate locations along the length of the image guide 26 as additional support means for aligning image guide 26 at the center of the endoscope sheath 24.

At the distal end 32, an end fitting 50 carries the objective lens assembly 34 in an abutting relationship with the end surface 23 of the image guide 26. The end fitting 50 also positions the objective lens 34 in a fixed relationship with respect to the window 33. In this particular embodiment, the fitting 50 abuts the window 33. A collar 52 centers the distal end of the image guide 26 in the endoscope sheath 24.

FIG. 3 therefore discloses an endoscope 30 as an example of a viewing scope that can utilize this invention. As will be apparent, the structure is simple to produce. There is no requirement for optically redesigning an image guide each time the length of an endoscope changes. Moreover, the image presented at the eyepiece 35 has a spatial resolution that is indistinguishable to a human eye over rigid optics with their greater cost and complexity over a significant range of magnifications. Although FIG. 3 discloses an endoscope, it will be apparent that a borescope will have the same general structure and will utilize an image guide in the same fashion.

Figure 4:
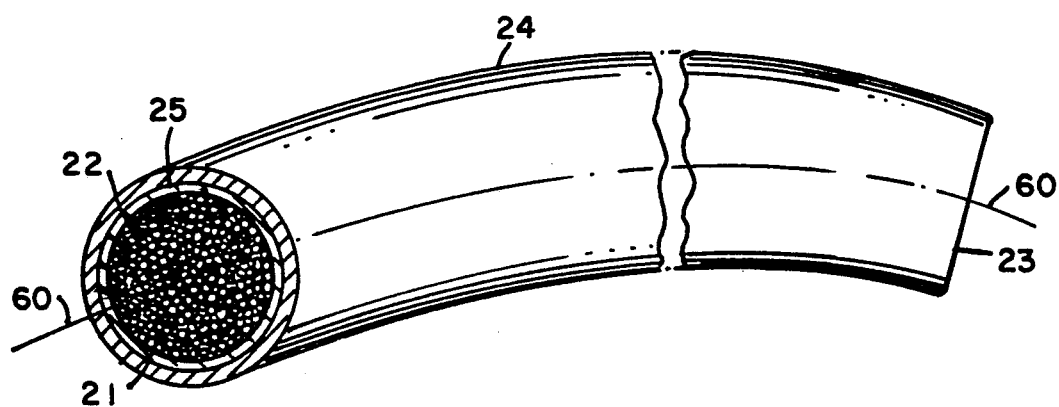
FIG. 4 is a view of an image guide constructed in accordance with this invention bent along a curved axis.

It has also been found that it is possible to produce an image guide with a curved shape as shown in FIG. 4. Specifically it has been found that an image guide 21, if heated, as for example over a Bunsen burner, can reach a temperature at which the sheath 24 and the rigid optical bundle 21 are sufficiently ductile to bend the entire structure along a curved axis 60 while maintaining collimation of the individual fibers between an end 22 and a remote end 23. This feature provides another degree of flexibility in the design of endoscopes, borescopes and other viewing scopes.

Thus, there has been disclosed an apparatus and a method that make use of a three-glass optical fiber to provide spatial resolution that surpasses the spatial resolution previously available with respect to image guides using optical fibers. The resulting spatial resolution approaches the spatial resolution of rigid optics and is not distinguished by the human eye over a wide range of image magnifications. This spatial resolution is realized with production costs of an image guide that are at most equal to or less than the cost of producing prior art fiber optic image guides. In an endoscope application the materials other than the rigid optical bundle 21 generally will comprise stainless steel and compatible adhesives. Other materials may be utilized in other applications particularly where sterilization is not required. The specifically disclosed embodiments show an image guide having a circular configuration. It will be apparent that other configurations might also be produced using an optical bundle formed in accordance with this invention.

Thus, while this invention has been disclosed in terms of certain embodiments, it will be apparent that many modifications can be made to the disclosed apparatus and method without departing from the invention. It is the intent of the appended claims to cover all such variations and modifications as come within the true spirit and scope of this invention.

What is claimed as new and desired to be secured by Letters Patent of the United States is:

1. In an optical system having means for forming an image and means for viewing the image at a position displaced from the image forming means, the improvement of rigid image guide means for transferring the image from the image forming means to the image viewing means, said image guide means comprising:

A. a fiber optic bundle including a plurality of substantially rigid optical fibers having a given length, each of said optical fibers having a central light transmitting and a concentric light reflecting layer for reflecting light into said central core, and encapsulating means encapsulating each of said optical fibers throughout said bundle for maintaining said plurality of optical fibers as a rigid bundle, and B. housing means for containing said rigid bundle of optical fibers with opposite ends thereof proximate the image forming means and image viewing means.

2. Image guide means as recited in claim 1 wherein said opposite ends of said rigid bundle are polished.

3. Image guide means as recited in claim 1 wherein said fiber optic bundle and said housing means lies along a curved axis.

4. Image guide means as recited in claim 1 wherein each of said optical fibers initially includes an outer concentric fusible layer along the length of said optical fiber, said fusible layer forming the encapsulating means.

5. Image guide means as recited in claim 4 wherein each of said optical fibers has a diameter less than 10 microns.

6. Image guide means as recited in claim 4 wherein said opposite ends of said rigid bundle are polished.

7. Image guide means as recited in claim 5 wherein said rigid bundle and said housing means lie along a curved axis.

8. A method for forming an image guide including a optical fiber bundle with proximal and distal end surfaces, said method comprising the steps of:
   A. drawing each of a plurality of optical fibers to a final diameter, each said optical fiber having a central light transmitting core and a concentric light reflecting layer for reflecting light into the central core,
   B. forming said plurality of fibers into an integral bundle, and
   C. encapsulating the position of each optical fiber throughout the bundle thereby to maintain its spatial position at either end of the bundle.

9. A method for forming an image guide as recited in claim 8 wherein each of the optical fibers includes an outer concentric layer of a fusible material and said encapsulating step includes heating the bundle until the outer layers of the plurality of optical fibers fuse together.

10. A method for forming an image guide as recited in claim 9 wherein said method forms an optical bundle of indefinite length and wherein said method additionally includes the steps of forming a bundle of finite length therefrom comprising:
   A. identifying an intermediate position along the bundle that is the finite length from an end thereof,
   B. cutting said integral bundle at the intermediate position, and
   C. polishing the exposed end portions of the optical bundle that are exposed by said cutting.

11. A method for forming an image guide as recited in claim 10 wherein the image guide includes a housing and wherein said method additionally includes the step of mounting the optical bundle in the housing.

12. A method for forming an image guide as recited in claim 11 wherein said method additionally includes the step of bending the housing and internal optical bundle along a curved axis.

13. In an optical viewing device useful in viewing an inner part of the body wherein said optical viewing device includes a tubular housing having proximal and distal ends, objective lens means at said distal end for forming an image of the inner part of the body and optical viewing means at said proximal end of said housing for enabling the image to be viewed externally to said body and said optical viewing device, the improvement of image guide means between said objective lens means and said optical viewing means comprising an optical fiber bundle formed of a plurality of optical fibers extending between said objective lens means and said optical viewing means for transferring the image from the distal end to the proximal end, each of said optical fibers having a central light transmitting core and an annular light reflecting layer for reflecting light into said central core and an encapsulating material for encapsulating each of said optical fibers throughout said bundle thereby to form a rigid bundle.

14. An optical viewing device as recited in claim 13 additionally comprising housing means for containing said rigid bundle of optical fibers with opposite ends thereof proximate said objective lens means and said optical viewing means.

15. An optical viewing device as recited in claim 14 wherein said opposite ends of said rigid bundle are polished.

16. An optical viewing device as recited in claim 14 wherein said rigid bundle and said housing means lie along a curved axis.

17. An optical viewing device as recited in claim 14 wherein each of said optical fibers initially includes an outer concentric fusible layer along the length of said optical fiber, said fusible layer forming said encapsulating material.

18. An optical viewing device as recited in claim 17 wherein each of said optical fibers has a diameter less than 10 microns.

19. An optical viewing device as recited in claim 18 wherein said opposite ends of said rigid bundle are polished.

20. An optical viewing device as recited in claim 19 wherein said rigid bundle and said housing means lie along a curved axis.

* * * * *